United States Patent
Yamaguchi et al.

(10) Patent No.: US 10,665,081 B2
(45) Date of Patent: May 26, 2020

(54) AWAKENING SUPPORT APPARATUS, AWAKENING SUPPORT METHOD AND AWAKENING SUPPORT PROGRAM

(71) Applicant: AISIN SEIKI KABUSHIKI KAISHA, Kariya-shi, Aichi-ken (JP)

(72) Inventors: Hideaki Yamaguchi, Okazaki (JP); Yoshihisa Suetsugu, Nagoya (JP)

(73) Assignee: AISIN SEIKI KABUSHIKI KAISHA, Kariya-shi, Aichi-ken (JP)

( * ) Notice: Subject to any disclaimer, the term of this patent is extended or adjusted under 35 U.S.C. 154(b) by 0 days.

(21) Appl. No.: 16/011,927

(22) Filed: Jun. 19, 2018

(65) Prior Publication Data
US 2019/0005797 A1    Jan. 3, 2019

(30) Foreign Application Priority Data
Jun. 29, 2017    (JP) .................. 2017-126941

(51) Int. Cl.
| | |
|---|---|
| G08B 21/06 | (2006.01) |
| B60Q 9/00 | (2006.01) |
| G06F 11/30 | (2006.01) |
| G06F 11/34 | (2006.01) |
| A61B 5/18 | (2006.01) |

(52) U.S. Cl.
CPC .............. *G08B 21/06* (2013.01); *A61B 5/18* (2013.01); *B60Q 9/00* (2013.01); *G06F 11/3013* (2013.01); *G06F 11/3438* (2013.01)

(58) Field of Classification Search
CPC .. G08B 21/06; B60Q 9/00; A61B 5/18; G06F 11/3013; G06F 11/3438
USPC ......................................................... 701/36
See application file for complete search history.

(56) References Cited

U.S. PATENT DOCUMENTS

| | | | | |
|---|---|---|---|---|
| 8,174,402 B2* | 5/2012 | Bouse | ............... | G05B 19/4065 340/635 |
| 8,725,311 B1* | 5/2014 | Breed | .................... | A61B 5/163 701/1 |
| 9,129,505 B2* | 9/2015 | Breed | ................ | G08B 21/0407 |

(Continued)

FOREIGN PATENT DOCUMENTS

| | | | | |
|---|---|---|---|---|
| EP | 3131074 A2 * | 2/2017 | .......... | B60K 28/066 |
| JP | 2005-186657 A | 7/2005 | | |

(Continued)

OTHER PUBLICATIONS

Hideaki Yamaguchi et al., "Effects of vibratory stimulation-induced kinesthetic illusions on driver's drowsiness", Proceedings of Technical Session Presentations in 2016 JSAE Annual Spring Congress, Society of Automotive Engineers of Japan, May 2016, No. 67-16S, pp. 1671-1676.

*Primary Examiner* — Atul Trivedi
(74) *Attorney, Agent, or Firm* — Sughrue Mion, PLLC

(57) ABSTRACT

An awakening support apparatus includes an acquisition portion acquiring surroundings information which indicates information of at least one of a temperature and a vibration around a driver of a movable object, a determination portion determining a drowsiness inducing level of the driver based on the surroundings information acquired by the acquisition portion, and an execution portion executing an awakening support for decreasing a possibility of induction of drowsiness of the driver based on a determination result of the drowsiness inducing level determined by the determination portion.

9 Claims, 10 Drawing Sheets

(56) References Cited

U.S. PATENT DOCUMENTS

| | | | |
|---|---|---|---|
| 9,637,133 B1* | 5/2017 | McCusker | A61B 5/02055 |
| 9,761,126 B2* | 9/2017 | Jensen | G01D 9/005 |
| 9,919,712 B1* | 3/2018 | Doyen | A61B 5/0022 |
| 2007/0280505 A1* | 12/2007 | Breed | B60W 40/08 |
| | | | 382/104 |
| 2009/0261979 A1* | 10/2009 | Breed | B60J 10/00 |
| | | | 340/576 |
| 2009/0268022 A1* | 10/2009 | Omi | A61B 5/18 |
| | | | 348/135 |
| 2011/0021866 A1* | 1/2011 | Iizuka | A61B 3/113 |
| | | | 600/26 |
| 2011/0105925 A1* | 5/2011 | Hatakeyama | A61B 5/0245 |
| | | | 600/509 |
| 2014/0062704 A1* | 3/2014 | Kubotani | G08B 21/06 |
| | | | 340/575 |
| 2014/0097957 A1* | 4/2014 | Breed | G08B 21/06 |
| | | | 340/576 |
| 2014/0139655 A1* | 5/2014 | Mimar | G08B 21/06 |
| | | | 348/77 |
| 2014/0276090 A1* | 9/2014 | Breed | A61B 5/18 |
| | | | 600/473 |
| 2014/0313309 A1* | 10/2014 | Matsuo | A61B 5/01 |
| | | | 348/78 |
| 2016/0001781 A1* | 1/2016 | Fung | B60R 25/25 |
| | | | 701/36 |
| 2016/0009295 A1* | 1/2016 | Chun | B60Q 5/005 |
| | | | 701/32.9 |
| 2016/0023666 A1* | 1/2016 | Lee | A61B 5/6893 |
| | | | 701/33.4 |
| 2016/0071393 A1* | 3/2016 | Kaplan | A61B 5/6831 |
| | | | 340/539.12 |
| 2017/0281068 A1* | 10/2017 | Zhang | A61M 21/00 |
| 2017/0291544 A1* | 10/2017 | Ishihara | B60K 35/00 |
| 2017/0313319 A1* | 11/2017 | Kishi | B60W 30/08 |
| 2018/0037236 A1* | 2/2018 | Yamaguchi | B60N 2/90 |
| 2019/0049955 A1* | 2/2019 | Yabuuchi | B60W 50/14 |
| 2019/0088104 A1* | 3/2019 | Crewe | B60Q 9/00 |
| 2019/0092167 A1* | 3/2019 | Kim | A61B 5/6893 |
| 2019/0092337 A1* | 3/2019 | Chua | B60W 50/16 |
| 2019/0184898 A1* | 6/2019 | Zheng | B60Q 9/00 |

FOREIGN PATENT DOCUMENTS

| | | | | |
|---|---|---|---|---|
| JP | 2007-233479 A | | 9/2007 | |
| JP | 2014-223271 A | | 12/2014 | |
| WO | WO-2015200224 A2 * | | 12/2015 | B60W 50/0098 |

* cited by examiner

FIG. 8

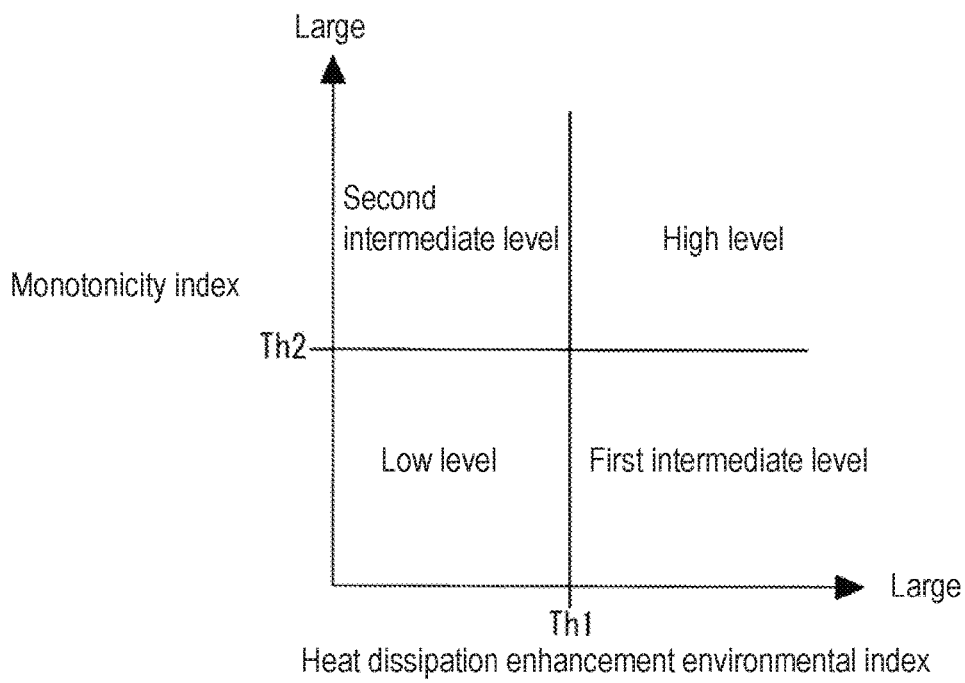

FIG. 9

| Drowsiness inducing level | Awakening support | |
|---|---|---|
| | Awakening stimulus | Caution message |
| Low level | — | — |
| Second intermediate level | Awakening stimulus for monotonicity | You are in monotonous driving conditions. Be careful of losing concentration on your driving. |
| First intermediate level | Awakening stimulus for heat dissipation | Your body temperature is easy to decrease at present. Ventilate an interior. |
| High level | Awakening stimulus for monotonicity and heat dissipation | You are easy to feel sleepy at present. Take a timely rest. |

US 10,665,081 B2

AWAKENING SUPPORT APPARATUS, AWAKENING SUPPORT METHOD AND AWAKENING SUPPORT PROGRAM

CROSS REFERENCE TO RELATED APPLICATIONS

This application is based on and claims priority under 35 U.S.C. § 119 to Japanese Patent Application 2017-126941, filed on Jun. 29, 2017, the entire content of which is incorporated herein by reference.

TECHNICAL FIELD

This disclosure generally relates to an awakening support apparatus, an awakening support method and an awakening support program.

BACKGROUND DISCUSSION

A technique for determining drowsiness of a driver of a vehicle based on physiological information such as a temperature of the driver, for example, and operation amount of the driver while the driver is driving the vehicle is known. Such technique is disclosed, for example, in JP2014-223271A, JP2007-233479A, JP2005-186657A and Hideaki Yamaguchi, et al., "Effects of Vibratory Stimulation-induced Kinesthetic Illusions on Driver's Drowsiness", Proceedings of Technical Session Presentations in 2016 JSAE Annual Spring Congress, Society of Automotive Engineers of Japan, May 2016, No. 67-16S, p. 1671-1676.

According to the aforementioned technique, expected drowsiness of the driver is not determinable, which may lead to difficulty in restraining occurrence of drowsiness, i.e., restraining drowsiness before it occurs.

A need thus exists for an awakening support apparatus, an awakening support method and awakening support program which is not susceptible to the drawback mentioned above.

SUMMARY

According to an aspect of this disclosure, an awakening support apparatus includes an acquisition portion acquiring surroundings information which indicates information of at least one of a temperature and a vibration around a driver of a movable object, a determination portion determining a drowsiness inducing level of the driver based on the surroundings information acquired by the acquisition portion, and an execution portion executing an awakening support for decreasing a possibility of induction of drowsiness of the driver based on a determination result of the drowsiness inducing level determined by the determination portion.

According to another aspect of this disclosure, an awakening support method includes acquiring surroundings information which indicates information of at least one of a temperature and a vibration around a driver of a movable object, determining a drowsiness inducing level of the driver based on the surroundings information, and executing an awakening support for decreasing a possibility of induction of drowsiness of the driver based on a determination result of the drowsiness inducing level.

According to a further aspect of this disclosure, a computer program product including programed instructions embodied in and stored on a non-transitory computer readable medium, wherein the instructions, when executed by a computer, cause the computer to perform acquiring surroundings information which indicates information of at least one of a temperature and a vibration around a driver of a movable object, determining a drowsiness inducing level of the driver based on the surroundings information, and executing an awakening support for decreasing a possibility of induction of drowsiness of the driver based on a determination result of the drowsiness inducing level.

BRIEF DESCRIPTION OF THE DRAWINGS

The foregoing and additional features and characteristics of this disclosure will become more apparent from the following detailed description considered with the reference to the accompanying drawings, wherein:

FIG. 8 is a diagram explaining a determination of drowsiness inducing level of the driver;

FIG. 9 is an example of an awakening support table correlating the drowsiness inducing level and awakening support to each other;

DETAILED DESCRIPTION

Figure 1:
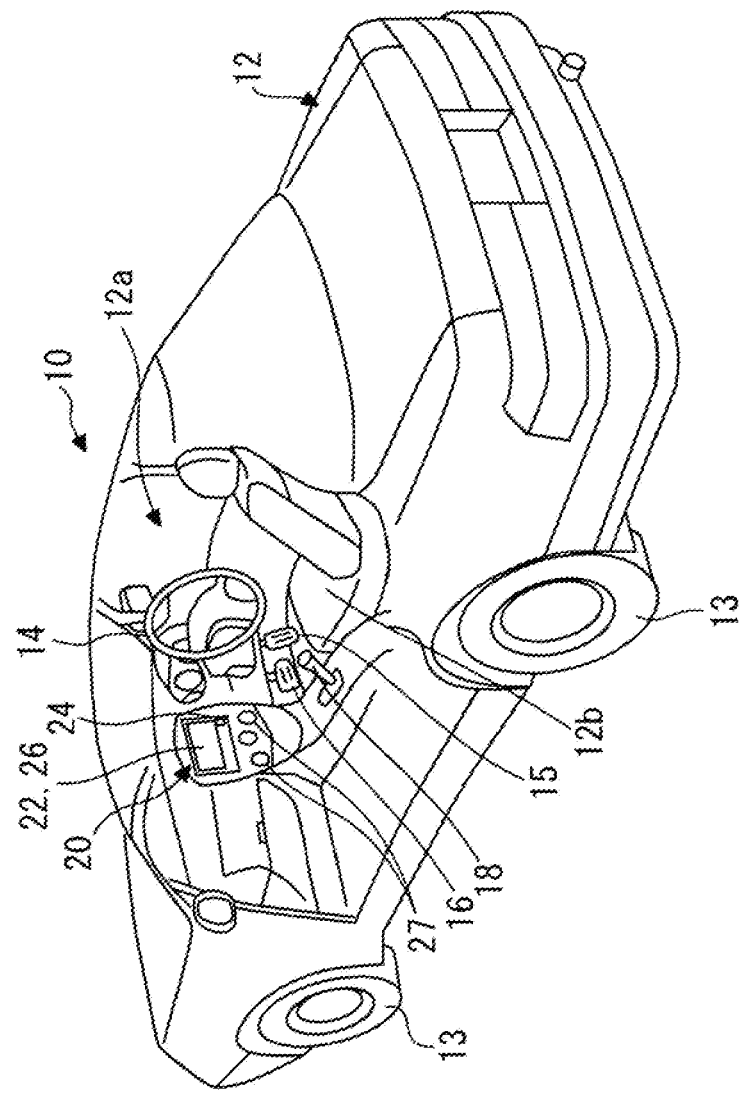
FIG. 1 is a perspective view illustrating an inside of a vehicle where an awakening support system according to embodiments in this disclosure is mounted.

Embodiments disclosed here are explained with reference to the attached drawings. The same or similar components through the embodiments bare the same reference numerals and duplicate explanation is omitted.

A first embodiment is explained with reference to the attached drawings. As illustrated in FIG. 1, a vehicle 10 serving as an example of a movable object may be an automobile driven by an internal combustion engine (engine) as a drive force, an automobile driven by an electric motor (motor) as the drive source, or a hybrid car driven by both the internal combustion engine and the electric motor as the drive sources. The vehicle 10 may include various types of transmissions and various types of apparatuses such as systems and components, for example, necessary for driving the internal combustion engine or the electric motor. In addition, system, number and layout of an apparatus for driving wheels 13 of the vehicle 10, for example, may be appropriately and variously specified.

As illustrated in FIG. 1, the vehicle 10 includes a vehicle body 12, the four wheels 13, a steering portion 14, an accelerating operation portion 15, a braking operation portion 16, a gear change operation portion 18, a monitor device 20 and an air conditioning device 27.

The vehicle body 12 constitutes a vehicle interior 12a where a passenger is in. The vehicle body 12 accommodates and holds, in the vehicle interior 12a, the steering portion 14, the accelerating operation portion 15, the braking operation portion 16, the gear change operation portion 18, the monitor device 20 and the air conditioning device 27, for example.

The four wheels 13 include the two front wheels 13 and the two rear wheels 13. The front wheels 13 function as steered wheels steered by the steering portion 14. The rear wheels 13 function as drive wheels rotated by the drive source.

The steering portion 14 is a steering wheel protruding from a dashboard, for example. The steering portion 14 changes a direction of the steered wheels (for example, the front wheels 13) by receiving an operation related to a traveling direction of the vehicle to right or left from a driver.

The accelerating operation portion 15 is an accelerator pedal positioned at the driver's foot, for example. The accelerating operation portion 15 accelerates the vehicle 10 by receiving an operation related to acceleration from the driver.

The braking operation portion 16 is a brake pedal positioned at the driver's foot, for example. The braking operation portion 16 decelerates the vehicle 10 by receiving an operation related to deceleration from the driver.

The gear change operation portion 18 is a shift lever protruding from a center console, for example. The gear change operation portion 18 changes the traveling direction between front and rear, for example, by receiving operations related to forward or rearward traveling direction and the gear change from the driver, for example.

The monitor device 20 is provided at a center portion in a vehicle width direction, i.e., in a left-right direction, of the dashboard, for example. The monitor device 20 may include a function as a navigation system or an audio system, for example. The monitor device 20 includes a display unit 22, an audio output unit 24 and an operation input portion 26. The monitor device 20 may include an operation input portion such as a switch, a dial, a joystick and a pressing button, for example.

The display unit 22 displays an image based on image information. The display unit 22 is a liquid crystal display (LCD) or an organic electroluminescent display (OELD), for example.

The audio output unit 24 outputs a sound based on audio data. The audio output unit 24 is a speaker, for example. The audio output unit 24 may be provided at a position other than the monitor device 20 within the vehicle interior 12a.

The operation input portion 26 receives an input from a user including the passenger or the driver. The operation input portion 26 is provided at a display surface of the display unit 22. The operation input portion 26 is a transparent touch panel so that the image of the display unit 22 is visible through the touch panel, for example. The operation input portion 26 receives an instruction via an input by the user who touches a position in the image displayed on a display screen of the display unit 22.

The air conditioning device 27 is an air conditioner including outlets provided at a center portion, left and right end portions of the dashboard, for example. The air conditioning device 27 generates airflow within the vehicle interior 12a and increases or decreases temperature at the vehicle interior 12a.

Figure 2:
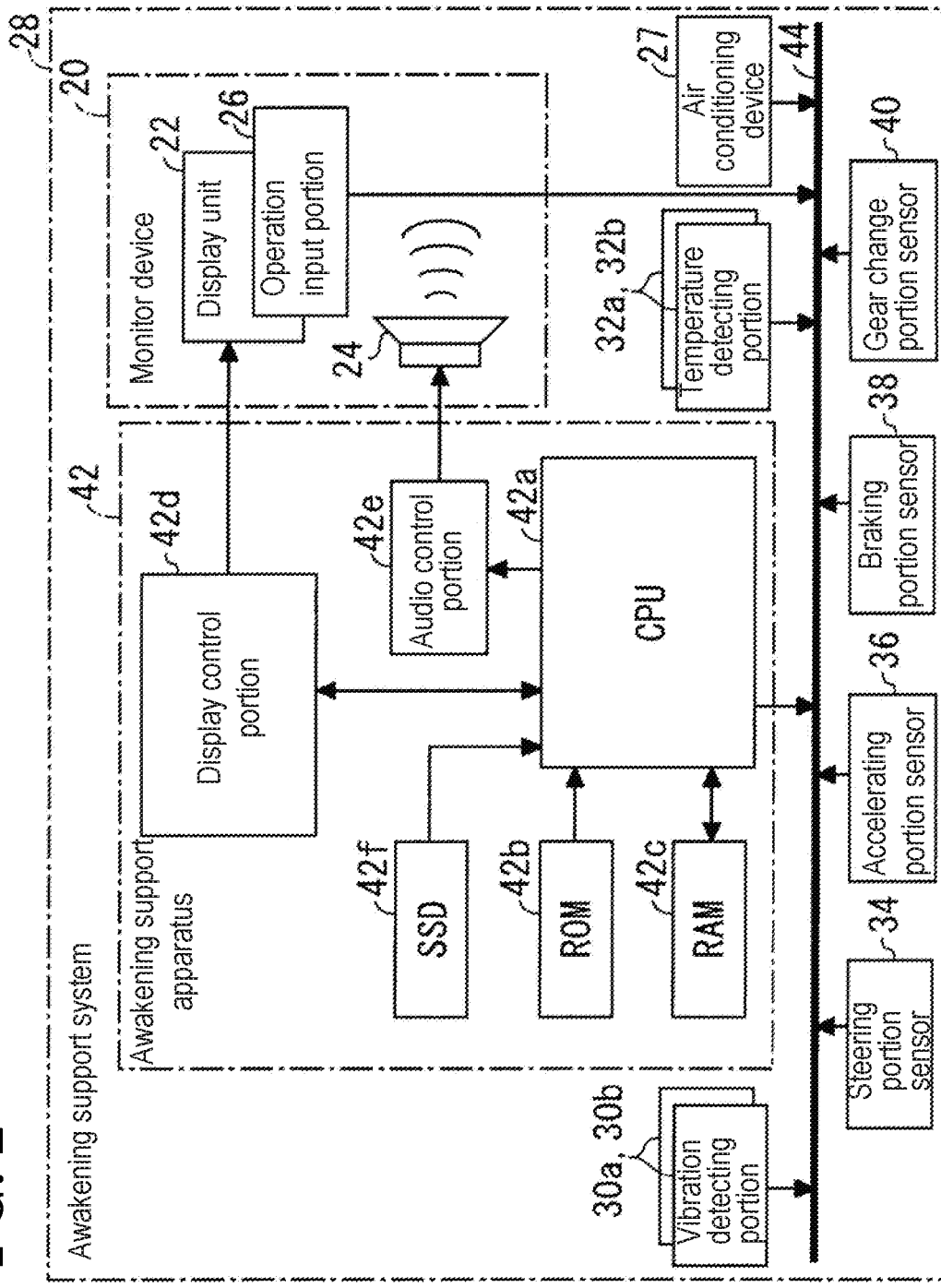
FIG. 2 is a block diagram explaining a hardware construction of a control system of the awakening support system mounted at the vehicle.

FIG. 2 is a block diagram explaining a hardware construction of a control system of an awakening support system 28 mounted at the vehicle 10. As illustrated in FIG. 2, the awakening support system 28 includes the monitor device 20, the air conditioning device 27, vibration detecting portions 30a, 30b, temperature detecting portions 32a, 32b, a braking portion sensor 38, an accelerating portion sensor 36, a steering portion sensor 34, a gear change portion sensor 40, an awakening support apparatus 42 and an in-vehicle network 44.

Each of the vibration detecting portions 30a and 30b is an acceleration sensor including a piezoelectric element, for example, to detect a vibration. The vibration detecting portions 30a and 30b are arranged in the vicinity of the driver such as at a seat 12b, for example, and at a portion with which the driver makes contact. The vibration detecting portions 30a and 30b detect vibrations in the vicinity of (i.e., around) the driver and transmitted to the driver. The vibration detecting portions 30a and 30b output vibration information indicating detected vibrations as a part of surroundings information to the awakening support apparatus 42 via the in-vehicle network 44. The vibration information includes information of intensity (strength) of vibration. The intensity of vibration is amplitude of vibration, for example. The vibration detecting portions 30a and 30b are hereinafter collectively referred to as a vibration detecting portion 30 in a case where the vibration detecting portions 30a and 30b are not necessary to be distinguished from each other.

Each of the temperature detecting portions 32a and 32b is a contact (contact type) temperature sensor which detects the temperature by a thermocouple and a thermistor, for example, or a non-contact (non-contact type) temperature sensor detecting the temperature based on heat radiation, for example. The temperature detecting portions 32a and 32b are arranged at the inside or in the vicinity of the seat 12b and in the vicinity of the driver. The temperature detecting portions 32a and 32b detect the temperature in the vicinity of (i.e., around) the driver and output temperature information indicating the detected temperature as a part of the surroundings information to the awakening support apparatus 42 via the in-vehicle network 44. The temperature detecting portions 32a and 32b are hereinafter collectively referred to as a temperature detecting portion 32 in a case where the temperature detecting portions 32a and 32b are not necessary to be distinguished from each other.

The steering portion sensor 34 is an angle sensor including a Hall element, for example, to detect a steering angle serving as a rotation angle of the steering portion 14. The steering portion sensor 34 outputs the detected steering angle of the steering portion 14 as operation information of the steering portion 14 to the awakening support apparatus 42 via the in-vehicle network 44.

The accelerating portion sensor 36 is a position sensor, for example, to detect the position of the accelerating operation portion 15 in a case where the accelerating operation portion 15 is the accelerator pedal. The accelerating portion sensor 36 outputs the detected position of the accelerating operation portion 15 as operation information of the accelerating operation portion 15 to the awakening support apparatus 42 via the in-vehicle network 44.

The braking portion sensor 38 is a position sensor, for example, to detect the position of the braking operation portion 16 in a case where the braking operation portion 16 is the brake pedal. The braking portion sensor 38 outputs the detected position of the braking operation portion 16 as operation information of the braking operation portion 16 to the awakening support apparatus 42 via the in-vehicle network 44.

The gear change portion sensor 40 is a position sensor, for example, to detect the position of the gear change operation portion 18 in a case where the gear change operation portion 18 is the shift lever. The gear change portion sensor 40 outputs the detected position of the gear change operation portion 18 as operation information of the gear change operation portion 18 to the awakening support apparatus 42 via the in-vehicle network 44.

The awakening support apparatus 42 is a computer such as an electronic control unit (ECU), for example. The awakening support apparatus 42 includes a central processing unit (CPU) 42a, a read only memory (ROM) 42b, a random access memory (RAM) 42c, a display control portion 42d, an audio control portion 42e and a solid state drive (SSD) 42f. The CPU 42a, the ROM 42b and the RAM 42c may be integrated in the same package.

The CPU 42a reads program stored at a non-volatile memory unit such as the ROM 42b, for example, to perform various calculation processing and controls based on the aforementioned program. The ROM 42b stores programs and parameters necessary for executing the programs. The RAM 42c temporarily stores various data used for calculation at the CPU 42a. The display control portion 42d mainly performs data conversion of image for display at the display unit 22 among the calculation processing performed at the awakening support apparatus 42. The audio control portion 42e mainly performs processing of audio for output from the audio output unit 24 among the calculation processing performed at the awakening support apparatus 42. The SSD 42f is a non-volatile memory portion which is rewritable, the SSD 42f holding data even when a power source of the awakening support apparatus 42 is turned off.

In the present embodiment, the awakening support apparatus 42 performs an entire control of the awakening support system 28 in a state where hardware and software (i.e., program) work together. For example, the awakening support apparatus 42 acquires the vibration information of the vibration detecting portion 30 and the temperature information of the temperature detecting portion 32 as the surroundings information. The awakening support apparatus 42 acquires the operation information from the sensors 34, 36 and 38. The awakening support apparatus 42 determines a drowsiness inducing level which indicates an expected drowsiness level of the driver in the future based on the surroundings information and the operation information and performs awakening support for decreasing possibility of drowsiness induction of the driver based on the determination result. The awakening support apparatus 42 performs the awakening support by transmitting an image or audio data as the awakening support to the monitor device 20, for example. The awakening support apparatus 42 transmits air-conditioning control information to the air conditioning device 27 to perform the awakening support, for example.

The in-vehicle network 44 is a controller area network (CAN) or a local interconnect network (LIN), for example. The in-vehicle network 44 electrically connects between the operation input portion 26, the air conditioning device 27, the vibration detecting portions 30a, 30b, the temperature detecting portions 32a, 32b, the steering portion sensor 34, the accelerating portion sensor 36, the braking portion sensor 38, the gear change portion sensor 40 and the awakening support apparatus 42 so that signals and information are transmittable and receivable between the aforementioned connected portions and sensors, for example.

Figure 3:
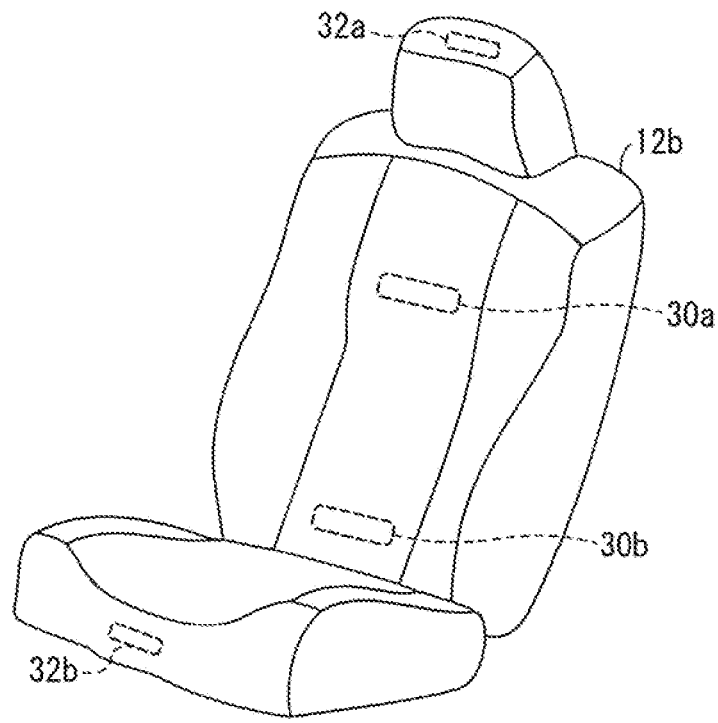
FIG. 3 is a perspective view of a seat for explaining arrangements of vibration detecting portions and temperature detecting portions.

FIG. 3 is a perspective view of the seat 12b for explaining arrangements of the vibration detecting portions 30a, 30b and the temperature detecting portions 32a, 32b. As illustrated in FIG. 3, the vibration detecting portions 30a and 30b are provided at a seatback of the seat 12b for the driver.

The vibration detecting portion 30a is provided at an upper portion of the seatback of the seat 12b, for example. Specifically, the vibration detecting portion 30a is provided in a region with which a surrounding portion of the shoulder blade (for example, the bottom corner portion of the shoulder blade) of the driver makes contact or in a surrounding portion of such region, for example. Accordingly, the vibration detecting portion 30a mainly detects the vibrations transmitted to the shoulder blade (for example, the bottom corner portion of the shoulder blade) of the driver.

The vibration detecting portion 30b is provided at a lower portion of the seatback of the seat 12b, for example. Specifically, the vibration detecting portion 30b is provided in a region with which the sacrum of the driver makes contact or in a surrounding portion of such region, for example. Accordingly, the vibration detecting portion 30b mainly detects the vibrations transmitted to the sacrum of the driver.

The temperature detecting portion 32a is provided at a headrest of the seat 12b, for example. The temperature detecting portion 32a mainly detects the temperature in the vicinity of the upper portion (for example, in the vicinity of the head portion) of the driver. At this time, the position where the temperature detecting portion 32a is arranged may not be limited to a specific position as long as the temperature detecting portion 32a detects the temperature in the vicinity of the upper portion of the driver. For example, in a case where the temperature detecting portion 32a is a non-contact temperature sensor, the sensor may be mounted at a ceiling of the vehicle 10 above the head portion of the driver.

The temperature detecting portion 32b is provided at a front end portion of a seat cushion (or a seating surface) of the seat 12b, for example. The temperature detecting portion 32b mainly detects the temperature in the vicinity of the lower portion (for example, in the vicinity of the leg portion) of the driver. That is, the temperature detecting portion 32b detects the temperature in the vicinity of the portion of the driver lower than the portion of the driver detected by the temperature detecting portion 32a. At this time, the position where the temperature detecting portion 32b is arranged may not be limited to a specific position as long as the temperature detecting portion 32b detects the temperature in the vicinity the lower portion of the driver. For example, in a case where the temperature detecting portion 32b is a non-contact temperature sensor, the sensor may be mounted at a floor surface of the vehicle 10 below the foot portion of the driver.

Figure 4:
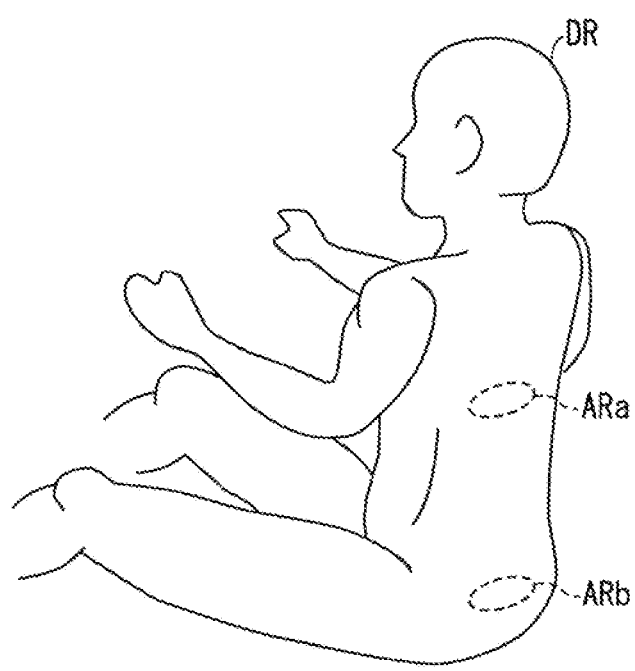
FIG. 4 is a perspective view of a driver's back for explaining areas in the back of the driver where vibrations are detected.

FIG. 4 is a perspective view of a driver's back for explaining areas in the back of the driver where the vibrations are detected. The vibration detecting portion 30a detects the vibrations transmitted to a region ARa in the vicinity of the shoulder blade (for example, the bottom corner of the shoulder blade) of the driver (driver DR) as illustrated in FIG. 4. The vibration detecting portion 30b detects the vibrations transmitted to a region ARb in the vicinity of the sacrum of the driver DR.

Next, an experimental result indicating a relationship between heat dissipation from a human body such as the driver DR, for example, and vibrations is explained.

Figure 5:
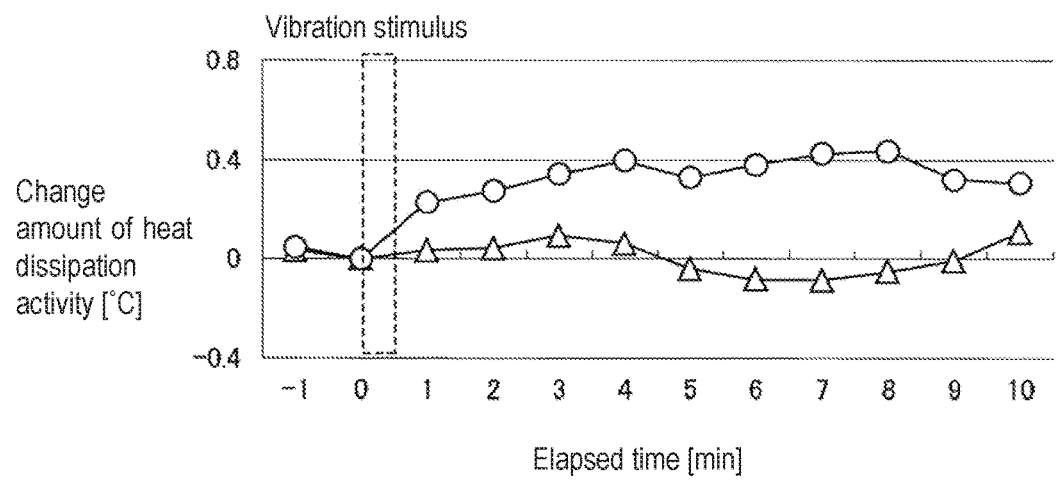
FIG. 5 is a diagram illustrating an experimental result of change amount of heat dissipation activity in a case where the vibrations are applied to the lower corner portion of the shoulder blade of the driver.

FIG. 5 is a diagram illustrating an experimental result of change amount of heat dissipation activity in a case where the vibrations are applied to the lower corner portion of the shoulder blade of the human body. In FIG. 5, a horizontal axis indicates time (i.e., elapsed time) and a vertical axis indicates a magnitude of change amount of heat dissipation activity. The change amount of heat dissipation activity corresponds to a change amount of heat dissipation of the human body which increases and decreases. The heat dissipation is enhanced with increase of change amount of heat dissipation activity. In addition, it is known that the increase of change amount of heat dissipation activity causes or induces drowsiness. A rectangle formed with a dotted line in FIG. 5 indicates a period of time during which the vibrations are applied to the bottom corner portion of the shoulder blade. In the experiment, vibrations with frequencies of 50 Hz were applied to the bottom corner portion of the shoulder blade of the human body for 30 seconds from time 0. The vibrations with frequencies of 50 Hz correspond to vibrations which may occur during a normal driving of the vehicle 10. In FIG. 5, a circle at each time indicates the change amount of heat dissipation activity of the human body to which the vibrations are applied while a triangle at each time indicates the change amount of heat dissipation activity of the human body to which the vibrations are not applied. As illustrated in FIG. 5, the change amount of heat dissipation activity of the human body to which the vibrations are applied to the bottom corner portion of the shoulder blade is greater than the change amount of heat dissipation activity of the human body to which the vibrations are not applied. That is, in a case where the vibrations are added to the bottom corner portion of the shoulder blade of the human body, the heat dissipation increases, which may highly possibly induce drowsiness. Thus, based on the vibrations added to the bottom corner portion of the shoulder blade of the driver DR, expected drowsiness of the driver DR is determinable.

Figure 6:
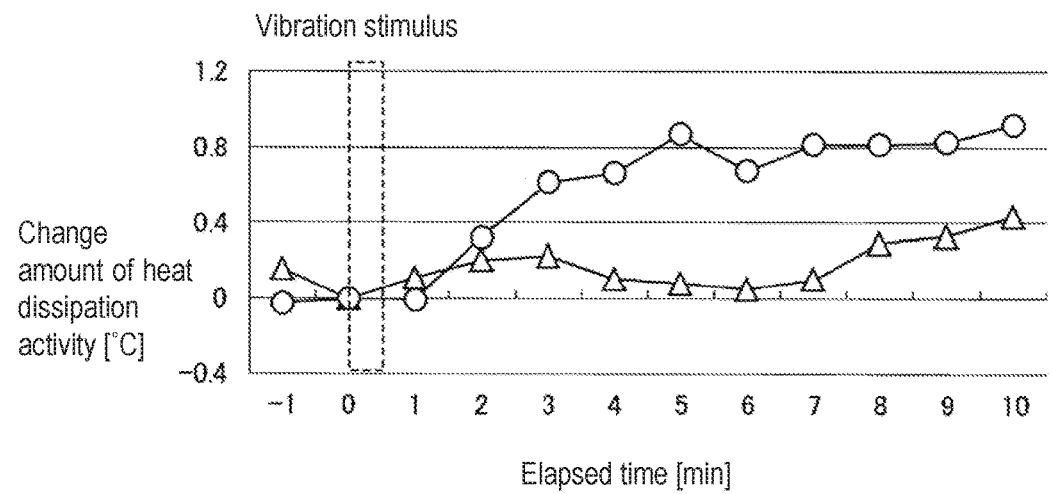
FIG. 6 is a diagram illustrating an experimental result of change amount of heat dissipation activity in a case where the vibrations are applied to the sacrum of the driver.

FIG. 6 is a diagram illustrating an experimental result of change amount of heat dissipation activity in a case where the vibrations are applied to the sacrum of the human body. In FIG. 6, a horizontal axis indicates time (i.e., elapsed time) and a vertical axis indicates a magnitude of change amount of heat dissipation activity. A rectangle formed with a dotted line in FIG. 6 indicates a period of time during which the vibrations are applied to the sacrum. In FIG. 6, a circle at each time indicates the change amount of heat dissipation activity of the human body to which the vibrations are applied while a triangle at each time indicates the change amount of heat dissipation activity of the human body to which the vibrations are not applied. In the experiment, the vibrations with frequencies of 50 Hz were applied to the sacrum of the human body for 30 seconds from time 0. As illustrated in FIG. 6, the change amount of heat dissipation activity of the human body to which the vibrations are applied to the sacrum is greater than the change amount of heat dissipation activity of the human body to which the vibrations are not applied. That is, in a case where the vibrations are added to the sacrum of the human body, the heat dissipation increases, which may highly possibly induce drowsiness. Thus, based on the vibrations added to the sacrum of the driver DR, expected drowsiness of the driver DR is determinable.

Figure 7:
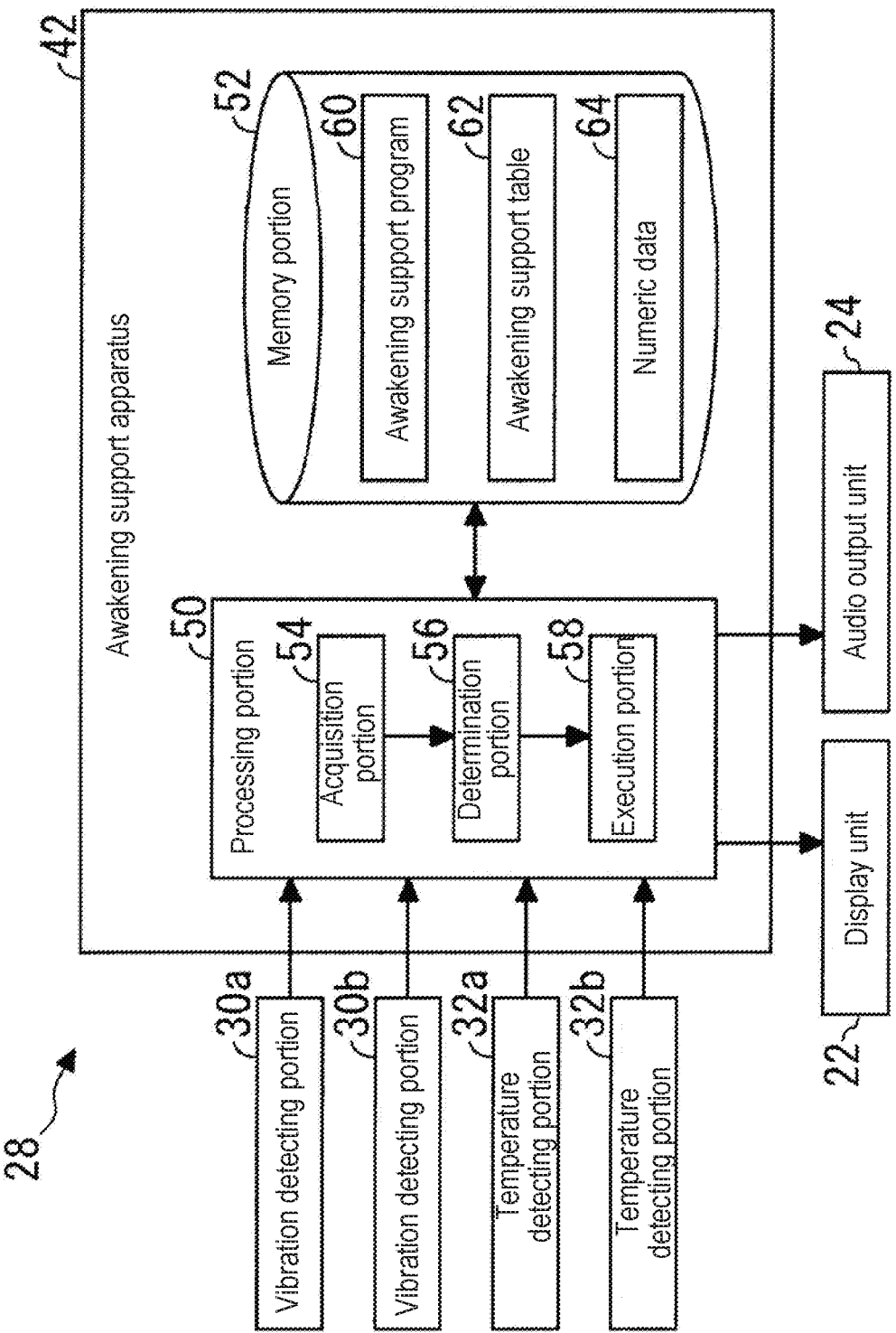
FIG. 7 is a functional block diagram explaining a function of an awakening support apparatus.

FIG. 7 is a functional block diagram explaining a function of the awakening support apparatus 42. As illustrated in FIG. 7, the awakening support apparatus 42 includes a processing portion 50 and a memory portion 52.

The processing portion 50 is achievable as a function of the CPU 42a, for example. The processing portion 50 includes an acquisition portion 54, a determination portion 56 and an execution portion 58. The processing portion 50 may read an awakening support program 60 stored at the memory portion 52 so as to include functions of the acquisition portion 54, the determination portion 56 and the execution portion 58, for example. The acquisition portion 54, the determination portion 56 and the execution portion 58 may be partially or entirely constituted by hardware of a circuit including an application specific integrated circuit (ASIC), for example.

The acquisition portion 54 acquires the surroundings information including the temperature information indicating the temperature in the vicinity of the driver DR from the temperature detecting portions 32a and 32b via the in-vehicle network 44. Specifically, the acquisition portion 54 acquires the surroundings information including the temperature information indicating the temperature in the vicinity of the upper portion of the driver DR from the temperature detecting portion 32a (which is hereinafter referred to as a first temperature) and the temperature information indicating the temperature in the vicinity of the lower portion of the driver DR from the temperature detecting portion 32b (which is hereinafter referred to as a second temperature). The acquisition portion 54 also acquires the surroundings information including the vibration information indicating the vibrations in the vicinity of the driver DR from the vibration detecting portions 30a and 30b via the in-vehicle network 44. Specifically, the acquisition portion 54 acquires the surroundings information including the vibration information indicating the vibrations in the vicinity of the shoulder blade of the driver DR from the vibration detecting portion 30a and the vibration information indicating the vibrations in the vicinity of the sacrum of the driver DR from the vibration detecting portion 30b. In a case where the vibration information and the temperature information are not necessary to be distinguished from each other, the vibration information and the temperature information are hereinafter collectively described as the surroundings information. The acquisition portion 54 acquires the operation information serving as information related to the operation of the vehicle 10 by the driver DR from each of the sensors 34, 36 and 38 via the in-vehicle network 44. The acquisition portion 54 outputs the acquired surroundings information including the vibration information and the temperature information and the acquired operation information to the determination portion 56.

The determination portion 56 determines the drowsiness inducing level of the driver DR. The drowsiness inducing level determined by the determination portion 56 includes an expected drowsiness inducing level of the driver DR in the future. That is, the drowsiness inducing level indicates whether or not the driver DR is in an environment of becoming drowsy, i.e., whether possibility of the driver DR feeling or becoming drowsiness is high or low. The determination portion 56 estimates or predicts future (expected)

drowsiness of the driver DR based on the drowsiness inducing level of the driver DR.

The determination portion 56 may determine the drowsiness inducing level of the driver DR based on the surroundings information. Specifically, the determination portion 56 may determine the drowsiness inducing level of the driver DR based on a heat dissipation enhancement environmental index HI calculated on a basis of the surroundings information. The heat dissipation enhancement environmental index HI is a value obtained by indexation of an environment which increases the heat dissipation of the human body and is a value for determining physiologically induced drowsiness by focusing on characteristics of thermoregulatory response of the human body. The thermoregulatory response is a physiological activity for securing constancy of temperature (body temperature) of body's interior (for example, a core body temperature).

As a temperature environment specific to the vehicle, a state where the temperature in the vicinity of the head portion of the driver is higher than the temperature in the vicinity of the leg (foot) portion of the driver is considered. In a case where the heat dissipation of the human body increases, i.e., blood distribution to distal portions such as hands and feet increases, the heat dissipation to the outside of the human body increases while the core body temperature decreases. It is known that increase in peripheral blood flow distribution and decrease in core body temperature induce drowsiness. At this time, the head portion (face) of the human body is sensitive to temperature stimulus and thus causes enhancement or suppression of the heat dissipation as thermoregulatory response in feedforward control so as to restrain increase or decrease in the core body temperature. Accordingly, in a case where a thermal environment is regulated on a basis of the temperature in the vicinity of the head portion so that the human (driver) feels comfortable, the blood distribution (blood flow distribution) to the distal portions (hands and feet) tends to increase. Because the temperature in the vicinity of the foot portion is low, the amount of heat dissipation to the outside of the human body tends to increase, which leads to decrease in the core body temperature. That is, a difference between the temperature in the vicinity of the head portion and the temperature in the vicinity of the foot portion is effective as an index of the drowsiness inducing level.

Accordingly, a temperature difference between the vicinity of the upper portion (for example, the head portion) of the human body and the vicinity of the lower portion (for example, the foot portion) of the human body and the vibrations applied to a specific portion (for example, the shoulder blade and the sacrum) of the human body are considered and specified as factors for inducing drowsiness because of enhancement of heat dissipation of the human body and decrease in the core body temperature.

The determination portion 56 according to the present embodiment determines the drowsiness inducing level based on a temperature difference which serves as a difference between the first temperature corresponding to the temperature of the upper portion of the driver DR and the second temperature corresponding to the temperature of the lower portion of the driver DR included in the surroundings information which is acquired by the acquisition portion 54. The determination portion 56 also determines the drowsiness inducing level based on the vibrations applied to the vicinity of the shoulder blade and the sacrum of the driver DR included in the surroundings information which is acquired by the acquisition portion 54. The determination portion 56 may calculate the heat dissipation enhancement environmental index HI based on a formula (1) including the temperature difference and the vibrations as below. The heat dissipation enhancement environmental index HI is derived from a degree of heat dissipation of the driver DR which is quantified on a basis of circumstances in the vicinity of the driver DR (for example, the temperature and the vibrations).

$$HI = \alpha 1 \times \Delta T + \alpha 2 \times VI1 + \alpha 3 \times VI2 \qquad (1)$$

α1, α2, α3: weight
ΔT: temperature difference (=Tu−Td)
Tu: first temperature (temperature in the vicinity of the upper portion (for example, the head portion) of the driver DR detected by the temperature detecting portion 32a)
Td: second temperature (temperature in the vicinity of the lower portion (for example, the foot portion) of the driver DR detected by the temperature detecting portion 32b
VI1: first vibration index (average value of vibration intensity in the vicinity of the shoulder blade (for example, the bottom corner of the shoulder blade) detected by the vibration detecting portion 30a)
VI2: second vibration index (average value of vibration intensity in the vicinity of the sacrum detected by the vibration detecting portion 30b)
The values α1, α2 and α3 may be appropriately specified beforehand.

The determination portion 56 may determine the drowsiness inducing level of the driver DR based on the operation information related to the operation of the vehicle 10 obtained by the acquisition portion 54 in addition to the surroundings information. The determination portion 56 may determine the drowsiness inducing level of the driver DR based on a monotonicity index SI calculated on a basis of a frequency of the operation of the vehicle 10 which is calculated on a basis of the operation information. The monotonicity index SI is a value obtained by indexation of monotonicity of time interval of driver's operation and is a value for determining driver's drowsiness based on fluctuation of time interval of the operation required for vehicle driving. The monotonicity index SI according to the embodiment is obtained by quantifying monotonicity of operations of the steering portion 14, the accelerating operation portion 15 and the braking operation portion 16. The monotonicity index SI increases with monotonicity of driving operation at the time of driving on an expressway or driving in a traffic jam, for example, which increases the drowsiness inducing level. The determination portion 56 may calculate the monotonicity index SI based on a formula (2) as below, for example.

$$SI = \beta 1 \times WF + \beta 2 \times AF + \beta 3 \times BF \qquad (2)$$

β1, β2, β3: weight
WF: steering operation frequency (inverse of variation in time intervals of operations of the steering portion 14)
AF: accelerating operation frequency (inverse of variation in time intervals of operations of the accelerating operation portion 15)
BF: braking operation frequency (inverse of variation in time intervals of operations of the braking operation portion 16)
The values β1, β2 and β3 may be appropriately specified beforehand.

Next, a method of calculating the steering operation frequency WF, the accelerating operation frequency AF and the braking operation frequency BF by the determination portion 56 is explained.

The determination portion 56 determines whether or not the driver DR operates the steering portion 14 based on the operation information of the steering portion 14 detected by the steering portion sensor 34, the operation information being obtained by the acquisition portion 54. In a case where the determination portion 56 determines that the driver DR operates the steering portion 14, a time at which the steering portion 14 is operated (which is hereafter referred to as a steering operation time) is stored at the memory portion 52. After storing plural steering operation times, the determination portion 56 calculates a time interval between the adjacent steering operation times (which is hereinafter referred to as a steering operation time interval). The determination portion 56 statistically calculates variation in steering operation time intervals based on standard deviation, for example, to calculate an inverse of the variation as the steering operation frequency WF.

The determination portion 56 stores a time at which the accelerating operation portion 15 is operated (which is hereafter referred to as an acceleration operation time) on a basis of the operation information of the accelerating operation portion 15 detected by the accelerating portion sensor 36, the operation information being obtained by the acquisition portion 54. The determination portion 56 calculates a time interval between the adjacent acceleration operation times in the plural acceleration operation times (which is hereinafter referred to as an accelerating operation time interval). The determination portion 56 statistically calculates variation in acceleration operation time intervals based on standard deviation, for example, to calculate an inverse of the variation as the accelerating operation frequency AF.

The determination portion 56 stores a time at which the braking operation portion 16 is operated (which is hereafter referred to as a braking operation time) on a basis of the operation information of the braking operation portion 16 detected by the braking portion sensor 38, the operation information being obtained by the acquisition portion 54. The determination portion 56 calculates a time interval between the adjacent braking operation times in the plural braking operation times (which is hereinafter referred to as a braking operation time interval). The determination portion 56 statistically calculates variation in braking operation time intervals based on standard deviation, for example, to calculate an inverse of the variation as the braking operation frequency BF.

The determination portion 56 determines the drowsiness inducing level of the driver DR based on the heat dissipation enhancement environmental index HI and the monotonicity index SI. The determination portion 56 outputs the determined drowsiness inducing level of the driver DR as a determination result to the execution portion 58.

The execution portion 58 performs the awakening support for decreasing possibility of induction of drowsiness of the driver DR based on the determination result of the drowsiness inducing level by the determination portion 56. For example, the execution portion 58 may output an image as the awakening support at the display unit 22. The execution portion 58 may output a sound as the awakening support at the audio output unit 24. The execution portion 58 may perform a temperature control within the vehicle interior 12a by the air conditioning device 27 as the awakening support. The execution portion 58 may perform the awakening support which is specified depending on the drowsiness inducing level of the driver DR. For example, the execution portion 58 may extract the awakening support related to the drowsiness inducing level of the driver DR from an awakening support table 62 stored at the memory portion 52.

The memory portion 52 is achievable as a function of at least one of the ROM 42b, the RAM 42c and the SSD 42f.

The memory portion 52 is achievable as a function of a memory unit on a network. The memory portion 52 stores program executed by the processing portion 50, data necessary for executing the program, and data generated by execution of the program, for example. The memory portion 52 stores the awakening support program 60 executed by the processing portion 50, for example. The memory portion 52 stores the awakening support table 62 necessary for performing the awakening support program 60. The memory portion 52 stores numeric data 64 including a threshold value for determination necessary for executing the awakening support program 60, for example. The memory portion 52 temporarily stores a value calculated through execution of the awakening support program 60.

FIG. 8 is a diagram explaining the determination of the drowsiness inducing level of the driver DR. In FIG. 8, a horizontal axis indicates the heat dissipation enhancement environmental index HI and a vertical axis indicates the monotonicity index SI.

As illustrated in FIG. 8, the determination portion 56 determines the drowsiness inducing level of the driver DR based on a first threshold value Th1 serving as a threshold value for the surroundings information and a second threshold value Th2 serving as a threshold value for the operation information. The first threshold value Th1 and the second threshold value Th2 may be specified beforehand and stored at the memory portion 52 as a part of the numeric data 64.

The determination portion 56 determines a first drowsiness inducing level of the driver DR by comparing the heat dissipation enhancement environmental index HI and the first threshold value Th1. For example, in a case where the heat dissipation enhancement environmental index HI is smaller than the first threshold value Th1, the determination portion 56 determines the first drowsiness inducing level to be a low level. In a case where the heat dissipation enhancement environmental index HI is equal to or greater than the first threshold value Th1, the determination portion 56 may determine the first drowsiness inducing level to be an intermediate level.

The determination portion 56 determines a second drowsiness inducing level of the driver DR by comparing the monotonicity index SI and the second threshold value Th2. For example, in a case where the monotonicity index SI is smaller than the second threshold value Th2, the determination portion 56 determines the second drowsiness inducing level to be a low level. In a case where the monotonicity index SI is equal to or greater than the second threshold value Th2, the determination portion 56 may determine the second drowsiness inducing level to be an intermediate level.

The determination portion 56 may determine the drowsiness inducing level of the driver DR to be a low level in a case where each of the first drowsiness inducing level and the second drowsiness inducing level is the low level. The determination portion 56 may determine the drowsiness inducing level of the driver DR to be a first intermediate level in a case where the first drowsiness inducing level is the intermediate level and the second drowsiness inducing level is the low level. The determination portion 56 may determine the drowsiness inducing level of the driver DR to be a second intermediate level in a case where the second drowsiness inducing level is the intermediate level and the first drowsiness inducing level is the low level. The determination portion 56 may determine the drowsiness inducing level of the driver DR to be a high level in a case where each of the first drowsiness inducing level and the second drowsiness inducing level is the intermediate level.

FIG. 9 is an example of the awakening support table 62 correlating the drowsiness inducing level and the awakening support to each other. As illustrated in FIG. 9, the awakening support table 62 which is stored at the memory portion 52 correlates the drowsiness inducing level of the driver DR determined by the determination portion 56 and the awakening support including a physical awakening stimulus and a caution message to each other. The execution portion 58 may extract at least one of the awakening stimulus and the caution message associated with the drowsiness inducing level from the awakening support table 62 as the awakening support.

Specifically, in a case where the execution portion 58 obtains the determination result indicating that the drowsiness inducing level is the second intermediate level from the determination portion 56, the execution portion 58 may perform the awakening support for the second intermediate level. An example of the awakening support for the second intermediate level is a driving sound from the audio output unit 24 and an application of awakening stimulus for monotonicity including a stimulus which imitates driving vibrations, for example. The execution portion 58 may adjust a level of driving sound and intensity of driving vibrations depending on values of the heat dissipation enhancement environmental index HI and the monotonicity index SI. Another example of the awakening support for the second intermediate level is an output of an image or a sound of caution message such as "You are in monotonous driving conditions. Be careful of losing concentration on your driving", for example.

The execution portion 58 may perform the awakening support for the first intermediate level in a case of obtaining the determination result indicating that the drowsiness inducing level is the first intermediate level from the determination portion 56. An example of the awakening support for the first intermediate level is an application of awakening stimulus for heat dissipation including airflow to the vicinity of the head portion of the driver DR by controlling the air conditioning device 27, for example. The execution portion 58 may adjust strength of airflow to the vicinity of the head portion depending on values of the heat dissipation enhancement environmental index HI and the monotonicity index SI. Another example of the awakening support for the first intermediate level is an output of an image or a sound of caution message such as "Your body temperature is easy to decrease at present. Ventilate an interior", for example.

The execution portion 58 may perform the awakening support for the high level in a case of obtaining the determination result indicating that the drowsiness inducing level is the high level. An example of the awakening support for the high level is an application of awakening stimulus for monotonicity, an application of awakening stimulus for heat dissipation, and decrease of temperature within the vehicle interior 12a. Another example of the awakening support for the high level is an output of an image or a sound of caution message such as "You are easy to feel sleepy at present. Take a timely rest", for example.

The execution portion 58 may not perform the awakening support in a case where the drowsiness inducing level is the low level.

Figure 10:
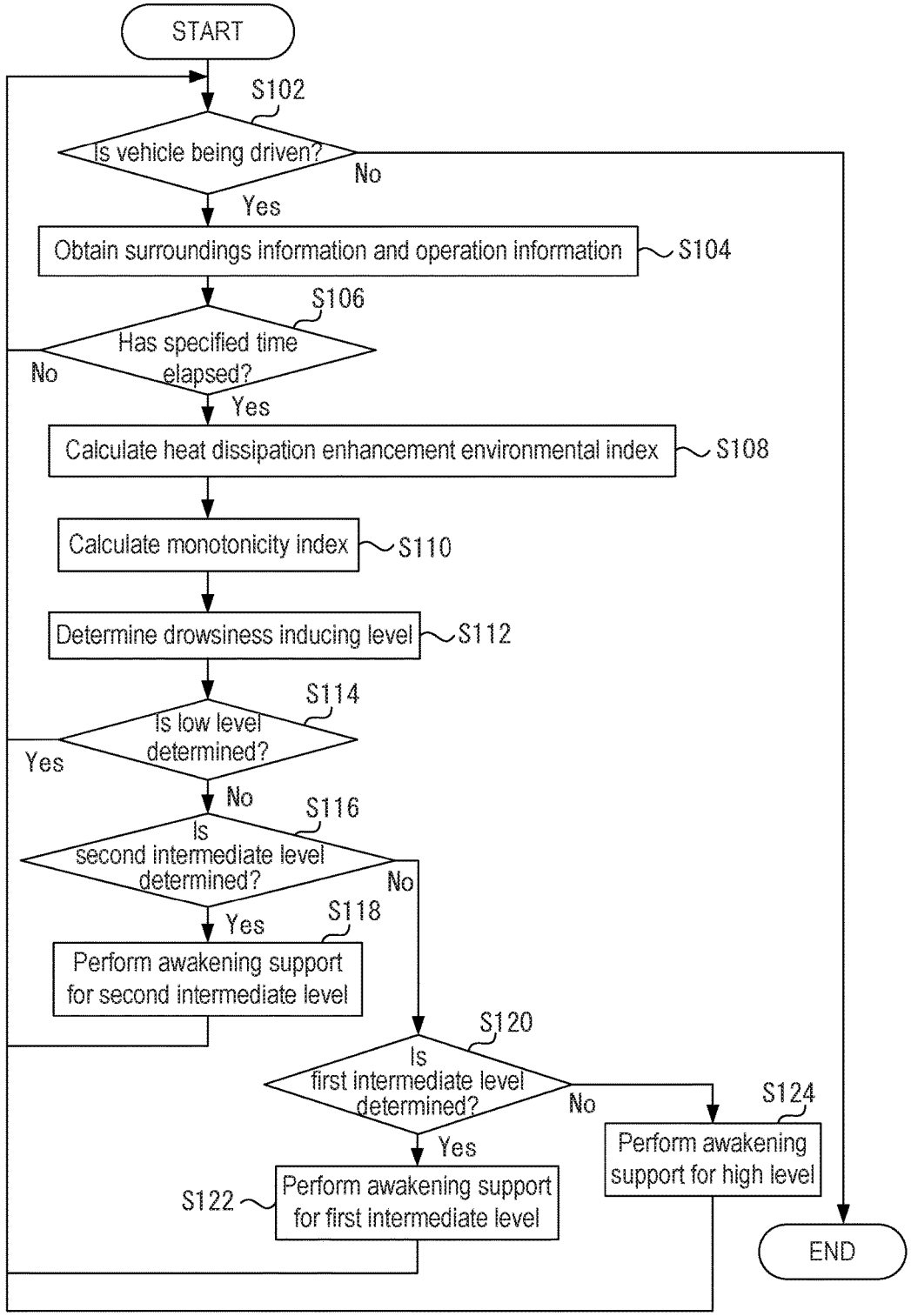
FIG. 10 is a flowchart of an awakening support process performed by a processing portion according to a first embodiment disclosed here.

FIG. 10 is a flowchart of an awakening support process performed by the processing portion 50 according to the first embodiment. The processing portion 50 performs the awakening support process by reading the awakening support program 60. The awakening support process is an example of an awakening support method.

As illustrated in FIG. 10, in the awakening support process, the acquisition portion 54 determines whether or not the vehicle 10 is being driven in step S102 (hereinafter "step" is omitted). In a case where it is determined that the vehicle 10 is not driven (No in S102), the awakening support process is terminated.

In a case where it is determined that the vehicle 10 is being driven (Yes in S102), the acquisition portion 54 obtains the surroundings information and the operation information in S104. The acquisition portion 54 then determines whether or not a specified time or more than the specified time has elapsed from a reference time (for example, from a time at which it is first determined that the vehicle is being driven) in S106. The specified time is a period of time during which the surroundings information and the operation information may be sufficiently obtained for calculating the heat dissipation enhancement environmental index HI and the monotonicity index SI so that the drowsiness inducing level is determinable. The specified time may be specified beforehand to be included in the numeric data 64. The operations in S102 and later are repeated until the specified time has elapsed (No in S106).

The acquisition portion 54 outputs the surroundings information and the operation information to the determination portion 56 when it is determined that the specified time has elapsed (Yes in S106).

The determination portion 56 calculates the heat dissipation enhancement environmental index HI based on the aforementioned formula (1) in S108 and the monotonicity index SI based on the aforementioned formula (2) in S110 when obtaining the surroundings information and the operation information. The determination portion 56 determines the drowsiness inducing level of the driver DR based on the calculated heat dissipation enhancement environmental index HI and monotonicity index SI in S112.

In a case where the determination portion 56 determines that the drowsiness inducing level is the low level (Yes in S114), the awakening support is not output from the execution portion 58 and the operations in S102 and later are repeated.

In a case where the determination portion 56 determines that the drowsiness inducing level is not the low level (No in S114) and is the second intermediate level (Yes in S116), the determination portion 56 outputs the determination result indicating that the drowsiness inducing level is the second intermediate level. The execution portion 58 then performs the awakening support for the second intermediate level when obtaining the aforementioned determination result in S118.

In a case where the determination portion 56 determines that the drowsiness inducing level is not the second intermediate level (No in S116) and is the first intermediate level (Yes in S120), the determination portion 56 outputs the determination result indicating that the drowsiness inducing level is the first intermediate level. The execution portion 58 then performs the awakening support for the first intermediate level when obtaining the aforementioned determination result in S122.

In a case where the determination portion 56 determines that the drowsiness inducing level is not the first intermediate level (No in S120), i.e., determines that the drowsiness inducing level is the high level, the determination portion 56 outputs the determination result indicating that the drowsiness inducing level is the high level. The execution portion 58 then performs the awakening support for the high level when obtaining the aforementioned determination result in S124.

After the operations in S118, S122 and S124, the processing portion 50 repeats the operations in S102 and later.

As mentioned above, according to the awakening support apparatus 42 of the first embodiment, the drowsiness inducing level of the driver DR is determined on a basis of the temperature and the vibrations in the vicinity of the driver DR which are related to drowsiness of the driver DR so as to perform the awakening support. Accordingly, the awakening support apparatus 42 may previously and accurately determine the drowsiness of the driver DR and perform the awakening support before biological reaction of the driver DR is weakened because of drowsiness and decrease of brain arousal level. Thus, occurrence of drowsiness itself may be restrained. For example, the awakening support apparats 42 may restrain or obviate drowsiness of the driver DR during automatic driving during which drowsiness is likely to be induced.

The awakening support apparatus 42 determines the drowsiness inducing level based on the temperature difference ΔT between the temperature at the upper portion (for example, the head portion) and the temperature at the lower portion (for example, the foot portion) of the driver DR which has a large relation with drowsiness of the driver DR. Thus, occurrence of drowsiness may be previously and accurately determined.

The awakening support apparatus 42 determines the drowsiness inducing level based on the vibrations (vibration conditions) at the shoulder blade and the sacrum of the driver DR among vibrations applied to the driver DR, the shoulder blade and the sacrum of the driver DR serving as portions where the enhancement of heat dissipation activity having a strong relation with occurrence of drowsiness is obtained. Thus, the aforementioned vibrations (vibration conditions) are optimum and effective as information for determining a possibility level of occurrence of drowsiness.

The awakening support apparatus 42 determines the drowsiness inducing level based on the monotonicity index SI calculated on a basis of variation in operation time intervals (for example, standard deviation) of the driver DR. Because the awakening support apparatus 42 determines the drowsiness inducing level based on the monotonicity index SI obtained by quantifying the monotonous operation which may induce drowsiness, accuracy in determining drowsiness (expected drowsiness) may improve while influence of driving road condition and personal difference such as a habit in driving operation of the driver DR, for example, is restrained.

In addition, the awakening support apparatus 42 determines the drowsiness inducing level of the driver DR based on both the heat dissipation enhancement environmental index HI calculated on a basis of the surroundings information related to the temperature and vibrations in the vicinity of the driver DR and the monotonicity index SI calculated on a basis of the operation information of the driver DR. Accordingly, because the awakening support apparatus 42 determines the drowsiness inducing level by two different indexes, accuracy in determining occurrence of drowsiness may further improve.

Because physiological information such as the body temperature of the driver and the operation amount of the driver are influenced by a surrounding weather and a driving speed, for example, accuracy in determining drowsiness may be difficult to be stabilized on a basis of the physiological information and the operation amount of the driver. Nevertheless, the awakening support apparatus 42 determines the drowsiness inducing level based on the heat dissipation enhancement environmental index HI and the monotonicity index SI which have a strong relation with induction of drowsiness. Thus, accuracy in determining occurrence of drowsiness may be stabilized.

A second embodiment which is obtained by modifying a part of the aforementioned awakening support processing according to the first embodiment is explained below.

Figure 11:
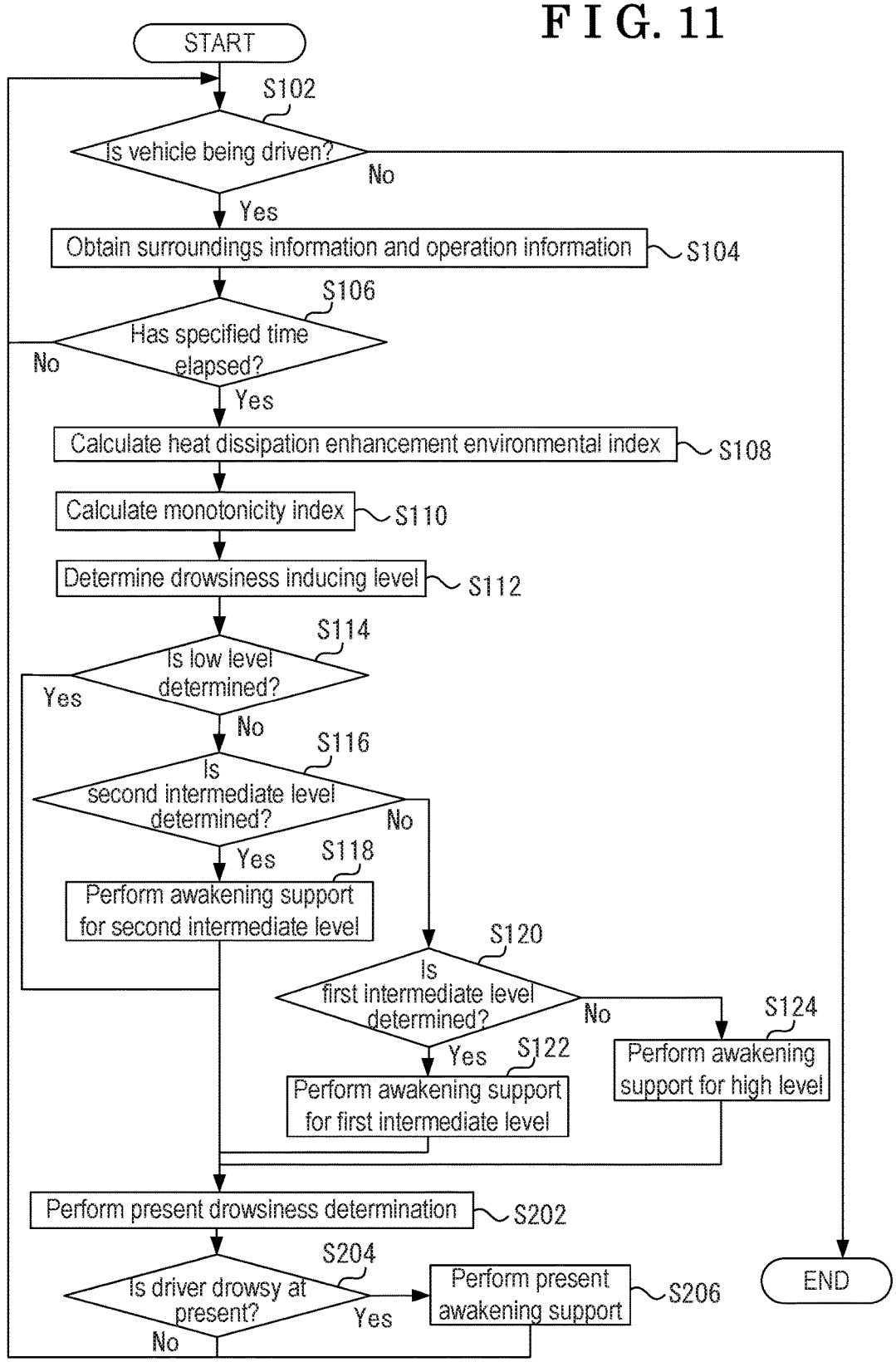
FIG. 11 is a flowchart of the awakening support process performed by the processing portion according to a second embodiment disclosed here.

FIG. 11 is a flowchart of awakening support process performed by the processing portion 50 according to the second embodiment. In FIG. 11, the same operations as the first embodiment bear the same step numbers and explanations thereof are simplified or omitted.

As illustrated in FIG. 11, after the processing portion 50 performs the operations from S102 to S112 and in a case where the determination portion 56 determines that the drowsiness inducing level is the low level (Yes in S114), the processing portion 50 performs a drowsiness determination for determining present drowsiness of the driver DR (i.e., a present drowsiness determination) in S202. In the same manner, in a case where the execution portion 58 performs the awakening support for the second intermediate level (S118), the awakening support for the first intermediate level (S122) or the awakening support for the high level (S124), the determination portion 56 performs the present drowsiness determination in S202.

The determination portion 56 may detect a movement of eyelid of the driver DR based on an image which captures the driver DR to thereby determine the present drowsiness of the driver DR based on blink frequency, for example. In a case where the determination portion 56 determines that the driver DR does not feel drowsy at present (No in S204), the operations in S102 and later are performed. In a case where the determination portion 56 determines that the driver DR feels drowsy at present (Yes in S204), the execution portion 58 performs a present awakening support in S206. For example, the execution portion 58 may perform the awakening support for the high level as the present awakening support. The execution portion 58 may also perform strengthened awakening support for the high level (for example, increasing output of driving sound or increasing airflow to the vicinity of the head portion) as the present awakening support. The processing portion 50 may thereafter perform the operations in S102 and later.

As mentioned above, the awakening support apparatus 42 determines the present drowsiness of the driver DR and performs the present awakening support based on the aforementioned determination result. The awakening support apparatus 42 according to the second embodiment may awake the driver DR even when the driver DR is in a state of drowsy or sleepy.

In the aforementioned first and second embodiments, the determination portion 56 determines the drowsiness inducing level of the driver DR based on simply the heat dissipation enhancement environmental index HI and the monotonicity index SI. Alternatively, in a third embodiment, the determination portion 56 determines the drowsiness inducing level of the driver DR based on the heat dissipation enhancement environmental index HI.

Figure 12:
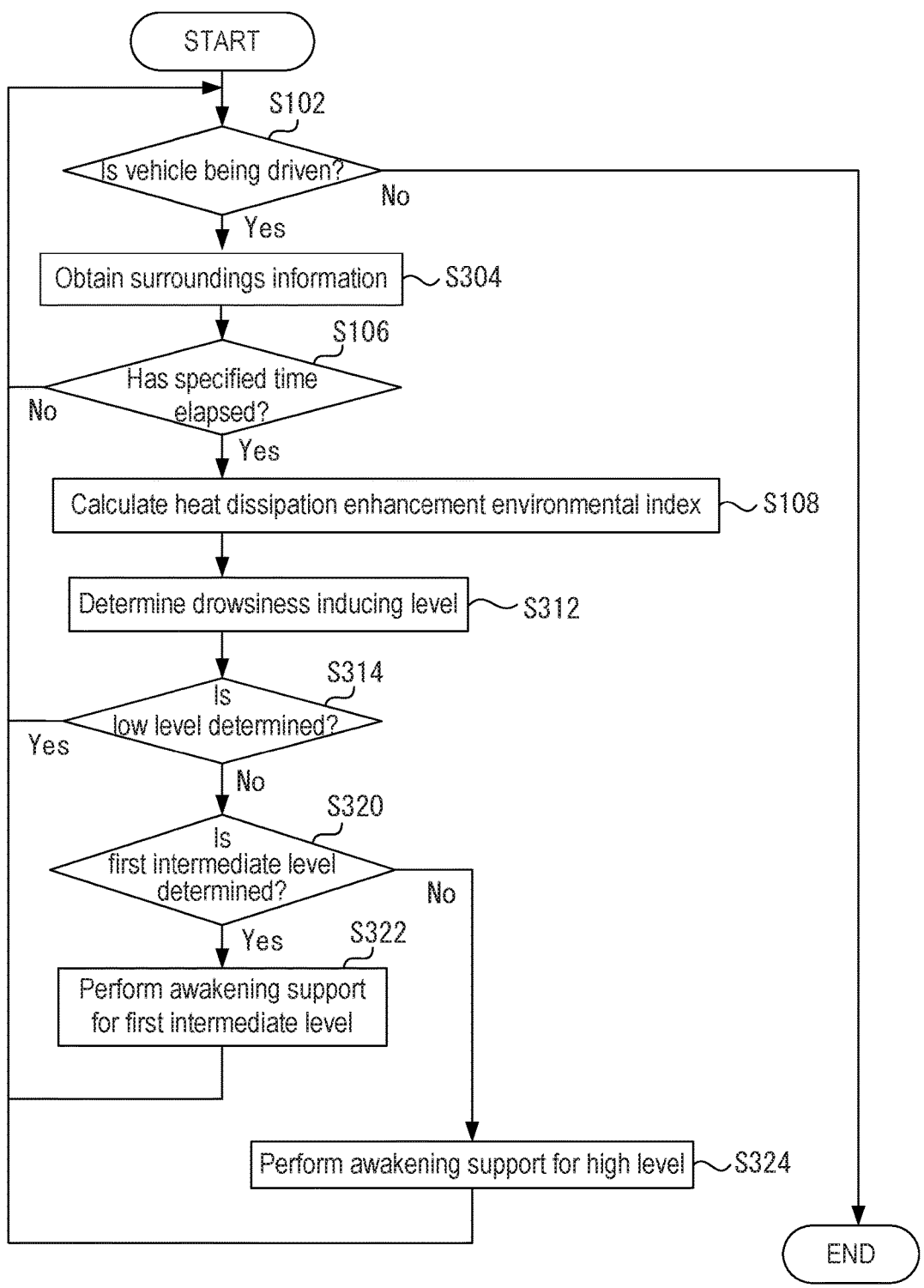
FIG. 12 is a flowchart of the awakening support process performed by the processing portion according to a third embodiment disclosed here.

FIG. 12 is a flowchart of awakening support process performed by the processing portion 50 according to the third embodiment. In FIG. 12, the same operations as the first embodiment bear the same step numbers and explanations thereof are simplified or omitted.

As illustrated in FIG. 12, according to the awakening support process of the third embodiment, the acquisition portion 54 obtains the surroundings information from the detecting portions 30a, 30b, 32a and 32b in S304 in a case where it is determined that the vehicle 10 is being driven (Yes in S102). When it is determined that the specified time has elapsed (Yes in S106), the acquisition portion 54 outputs the obtained surroundings information to the determination portion 56. The determination portion 56 calculates the heat dissipation enhancement environmental index HI based on the obtained surroundings information in S108. The determination portion 56 determines the drowsiness inducing level based on the aforementioned heat dissipation enhancement environmental index HI in S312.

In a case where the determination portion 56 determines that the drowsiness inducing level is the low level based on the heat dissipation enhancement environmental index HI (Yes in S314), the operations in S102 and later are repeated.

In a case where the determination portion 56 determines that the drowsiness inducing level is the first intermediate level (Yes in S320), the execution portion 58 performs the awakening support for the first intermediate level in S322. Afterwards, the operations in S102 and later are repeated.

In a case where the determination portion 56 determines that the drowsiness inducing level is not the first intermediate level (No in S320), the execution portion 58 performs the awakening support for the high level in S324. Afterwards, the operations in S102 and later are repeated.

A method of determining the drowsiness inducing level at the determination portion 56 according to the third embodiment is explained below.

Figure 13:
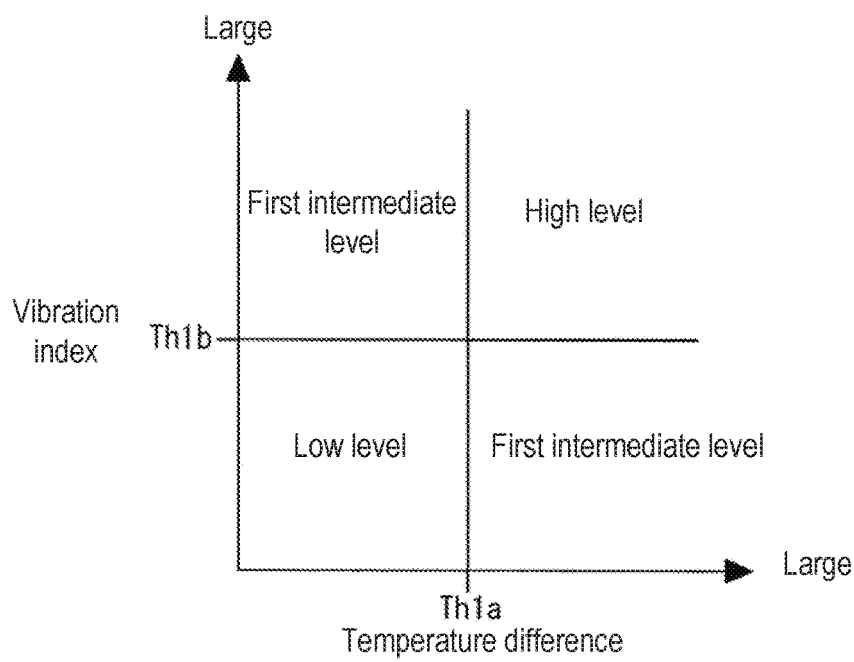
FIG. 13 is a diagram explaining a first determination method for determining the drowsiness inducing level by the determination portion according to the third embodiment.

FIG. 13 is a diagram explaining a first determination method of the drowsiness inducing level at the determination portion 56 according to the third embodiment. In FIG. 3, a horizontal axis indicates the temperature difference $\Delta T$ and a vertical axis indicates a vibration index. The vibration index of the vertical axis may be one of the first vibration index VI1, the second vibration index VI2 and an average between the first vibration index and the second vibration index $(=(VI1+VI2)/2)$. In the following, in a case where the first vibration index VI1, the second vibration index VI2 and the average therebetween are not necessary to be distinguished from one another, the vibration index is collectively described as the vibration index VI.

As illustrated in FIG. 13, in a case where the temperature difference $\Delta T$ is smaller than a temperature threshold value Th1$a$ and the vibration index VI is smaller than a vibration threshold value Th1$b$, the determination portion 56 determines the drowsiness inducing level of the driver DR to be the low level. In a case where the temperature difference $\Delta T$ is equal to or greater than the temperature threshold value Th1$a$ or the vibration index VI is equal to or greater than the vibration threshold value Th1$b$, the determination portion 56 determines the drowsiness inducing level of the driver DR to be the first intermediate level. In a case where the temperature difference $\Delta T$ is equal to or greater than the temperature threshold value Th1$a$ and the vibration index VI is equal to or greater than the vibration threshold value Th1$b$, the determination portion 56 determines the drowsiness inducing level of the driver DR to be the high level.

Figure 14:
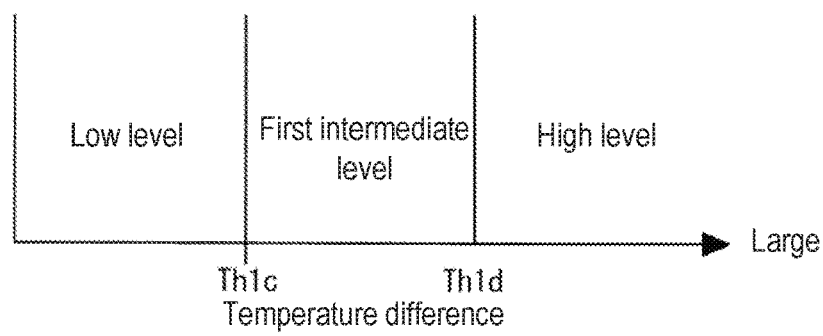
FIG. 14 is a diagram explaining a second determination method for determining the drowsiness inducing level by the determination portion according to the third embodiment.

FIG. 14 is a diagram explaining a second determination method of the drowsiness inducing level at the determination portion 56 according to the third embodiment. In FIG. 14, a horizontal axis indicates the temperature difference $\Delta T$. As illustrated in FIG. 14, the determination portion 56 may determine the drowsiness inducing level based on the temperature difference $\Delta T$ without using the vibration index VI. Specifically, in a case where the temperature difference $\Delta T$ is smaller than a first temperature difference threshold value Th1$c$, the determination portion 56 determines the drowsiness inducing level of the driver DR to be the low level. In a case where the temperature difference $\Delta T$ is equal to or greater than the first temperature difference threshold value Th1$c$ and is smaller than a second temperature difference threshold value Th1$d$, the determination portion 56 determines the drowsiness inducing level of the driver DR to be the first intermediate level. The second temperature difference threshold value Th1$d$ is greater than the first temperature difference threshold value Th1$c$. In a case where the temperature difference $\Delta T$ is equal to or greater than the second temperature difference threshold value Th1$d$, the determination portion 56 determines the drowsiness inducing level of the driver DR to be the high level.

Figure 15:
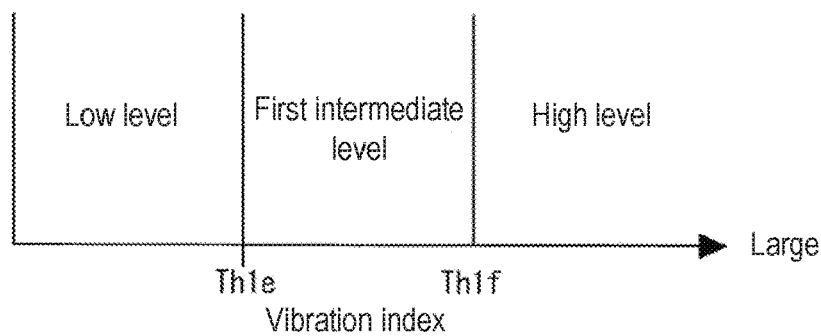
FIG. 15 is a diagram explaining a third determination method for determining the drowsiness inducing level by the determination portion according to the third embodiment.

FIG. 15 is a diagram explaining a third determination method of the drowsiness inducing level at the determination portion 56 according to the third embodiment. In FIG. 15, a horizontal axis indicates the vibration index VI. As illustrated in FIG. 15, the determination portion 56 may determine the drowsiness inducing level based on the vibration index VI without using the temperature difference $\Delta T$. At this time, the vibration index VI may be one of the first vibration index VI1, the second vibration index VI2 and the average between the first vibration index and the second vibration index $(=(VI1+VI2)/2)$. Specifically, in a case where the vibration index VI is smaller than a first vibration threshold value Th1$e$, the determination portion 56 determines the drowsiness inducing level of the driver DR to be the low level. In a case where the vibration index VI is equal to or greater than the first vibration threshold value Th1$e$ and is smaller than a second vibration threshold value Th1$f$, the determination portion 56 determines the drowsiness inducing level of the driver DR to be the first intermediate level. The second vibration threshold value Th1$f$ is greater than the first vibration threshold value Th1$e$. In a case where the vibration index VI is equal to or greater than the second vibration threshold value Th1$f$, the determination portion 56 determines the drowsiness inducing level of the driver DR to be the high level.

Functions, connection relations, quantities and arrangements of the constructions or components in each of the aforementioned embodiments may be appropriately modified or omitted, for example. The embodiments may be appropriately combined to one another. An order of steps in the awakening support process in each of the embodiments may be appropriately changed.

In the aforementioned embodiments, the vehicle 10 is the example of the movable object. The movable object may be other than the vehicle 10 as long as including a drive source such as an internal combustion engine and an electric motor, for example, and is movable by itself. For example, the movable object may be an airplane or a vessel, for example.

In the aforementioned embodiments, information related to the operations of the steering portion 14, the accelerating operation portion 15 and the braking operation portion 16 serves as the example of the operation information. Alternatively, the operation information may include information related to the operation of the gear change operation portion 18, for example.

According to the aforementioned embodiments, the awakening support apparatus 42 includes the acquisition portion 54 acquiring surroundings information which indicates information of at least one of the temperature and the vibration around the driver DR of the vehicle 10 (movable object), the determination portion 56 determining the drowsiness inducing level of the driver DR based on the surroundings information acquired by the acquisition portion 54, and the execution portion 58 executing the awakening support for decreasing a possibility of induction of drowsiness of the driver DR based on the determination result of the drowsiness inducing level determined by the determination portion 56.

Accordingly, because the awakening support apparatus 42 determines the drowsiness inducing level of the driver DR based on the temperature or the vibration around the driver DR, accuracy in determining drowsiness (expected drowsiness) of the driver DR may improve to thereby restrain or obviate occurrence of drowsiness itself.

In addition, the acquisition portion 54 acquires the surroundings information indicating the first temperature around the upper portion of the driver DR and the second temperature around the lower portion of the driver DR. The determination portion 56 determines the drowsiness inducing level based on the temperature difference ΔT between the first temperature and the second temperature.

Accordingly, because the awakening support apparatus 42 determines the drowsiness inducing level of the driver DR based on the difference between the temperature around the upper portion of the driver and the temperature around the lower portion of the driver, the temperature difference having a large relation with the drowsiness of the driver DR, accuracy in determining drowsiness may further improve.

Further, the acquisition portion 54 acquires the surroundings information indicating the vibration around the shoulder blade and the sacrum of the driver DR. The determination portion 56 determines the drowsiness inducing level based on the vibration acquired by the acquisition portion 54.

Accordingly, because the awakening support apparatus 42 employs the vibration (vibration condition) of the shoulder blade and the sacrum of the driver DR among vibrations applied to the driver DR for the determination, the shoulder blade and the sacrum of the driver DR serving as portions where enhancement of heat dissipation activity having a strong relation with occurrence of drowsiness is obtained, the aforementioned vibration (vibration condition) is optimum and effective as information for determining a possibility level of occurrence of drowsiness.

Furthermore, the acquisition portion 54 acquires the operation information related to operations of the vehicle 10 by the driver DR. The determination portion 56 determines the drowsiness inducing level based on the monotonicity index SI calculated on a basis of a variation in time intervals of the operations of the driver DR.

Accordingly, because the awakening support apparatus 42 determines the drowsiness inducing level of the driver DR based on the monotonicity index SI obtained by quantifying a monotonous operation which is easy to induce drowsiness, accuracy in determining drowsiness may further improve.

Furthermore, the determination portion 56 determines the drowsiness inducing level based on a combination of the surroundings information and the monotonicity index SI.

The awakening support apparatus 42 determines the drowsiness inducing level of the driver DR based on both the surroundings information related to the temperature or vibration around the driver DR and the monotonicity index SI calculated on a basis of the operation information of the driver DR. Accordingly, because the awakening support apparatus 42 determines the drowsiness inducing level by two different indexes, accuracy in determining occurrence of drowsiness may further improve.

Furthermore, the acquisition portion 54 acquires the surroundings information indicating the first temperature around the upper portion of the driver DR and the second temperature around the lower portion of the driver DR. The determination portion 56 determines the drowsiness inducing level based on the temperature difference ΔT between the first temperature and the second temperature and the monotonicity index SI.

The awakening support apparatus 42 determines the drowsiness inducing level of the driver DR based on both the temperature difference between the first temperature and the second temperature and the monotonicity index SI calculated on a basis of the operation information of the driver DR. Accordingly, because the awakening support apparatus 42 determines the drowsiness inducing level by two different indexes, accuracy in determining occurrence of drowsiness may further improve.

Furthermore, the acquisition portion 54 acquires the surroundings information indicating the vibration around the shoulder blade and the sacrum of the driver DR. The determination portion 56 determines the drowsiness inducing level based on a combination of the vibration acquired by the acquisition portion 54 and the monotonicity index SI.

The awakening support apparatus 42 determines the drowsiness inducing level of the driver DR based on both the vibration around the shoulder blade and the sacrum of the driver DR and the monotonicity index SI calculated on a basis of the operation information of the driver DR. Accordingly, because the awakening support apparatus 42 determines the drowsiness inducing level by two different indexes, accuracy in determining occurrence of drowsiness may further improve.

Furthermore, the execution portion 58 performs the awakening support correlated to the surroundings information in a case where it is determined that the surroundings information is greater than the first threshold value Th1 as the drowsiness inducing level and performs the awakening support correlated to the monotonicity index SI in a case where it is determined that the monotonicity index SI is greater than the second threshold value Th2 as the drowsiness inducing level.

Accordingly, because the awakening support apparatus 42 determines the drowsiness inducing level by two different indexes, accuracy in determining occurrence of drowsiness may further improve.

According to the aforementioned embodiments, the awakening support method includes acquiring surroundings information which indicates information of at least one of the temperature and the vibration around the driver DR of the vehicle 10 (movable object), determining the drowsiness inducing level of the driver DR based on the surroundings information, and executing the awakening support for decreasing a possibility of induction of drowsiness of the driver DR based on the determination result of the drowsiness inducing level.

Accordingly, because the awakening support apparatus 42 determines the drowsiness inducing level of the driver DR based on the temperature or the vibration around the driver DR, accuracy in determining drowsiness (expected drowsiness) of the driver DR may improve to thereby restrain or obviate occurrence of drowsiness itself.

According to the aforementioned embodiments, a computer program product including programed instructions embodied in and stored on a non-transitory computer readable medium, wherein the instructions, when executed by a computer, cause the computer to perform acquiring surroundings information which indicates information of at least one of the temperature and the vibration around the driver DR of the vehicle 10 (movable object), determining the drowsiness inducing level of the driver DR based on the surroundings information, and executing the awakening support for decreasing a possibility of induction of drowsiness of the driver DR based on the determination result of the drowsiness inducing level.

Accordingly, because the awakening support apparatus 42 determines the drowsiness inducing level of the driver DR based on the temperature or the vibration around the driver DR, accuracy in determining drowsiness (expected drowsiness) of the driver DR may improve to thereby restrain or obviate occurrence of drowsiness itself.

The principles, preferred embodiment and mode of operation of the present invention have been described in the foregoing specification. However, the invention which is intended to be protected is not to be construed as limited to the particular embodiments disclosed. Further, the embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

The invention claimed is:

1. An awakening support apparatus comprising:
an acquisition portion acquiring surroundings information which indicates information of a temperature around a driver of a movable object and a vibration applied to a specific portion of the driver;
a determination portion determining a drowsiness inducing level of the driver based on an enhancement environmental index indicating a heat dissipation of the driver, enhancement environmental index being calculated on a basis of the temperature and the vibration included in the surroundings information acquired by the acquisition portion; and
an execution portion executing an awakening support for decreasing a possibility of induction of drowsiness of the driver based on a determination result of the drowsiness inducing level determined by the determination portion.

2. The awakening support apparatus according to claim 1, wherein
the acquisition portion acquires the surroundings information indicating a first temperature around an upper portion of the driver and a second temperature around a lower portion of the driver,
the determination portion determines the drowsiness inducing level based on the enhancement environmental index calculated on a basis of a temperature difference between the first temperature and the second temperature.

3. The awakening support apparatus according to claim 1, wherein
the acquisition portion acquires the surroundings information indicating the vibration around a shoulder blade and a sacrum of the driver,
the determination portion determines the drowsiness inducing level based on the enhancement environmental index calculated on a basis of the vibration acquired by the acquisition portion.

4. The awakening support apparatus according to claim 1, wherein
the acquisition portion acquires operation information related to operations of the movable object by the driver,
the determination portion determines the drowsiness inducing level based on the enhancement environmental index and a monotonicity index calculated on a basis of a variation in time intervals of the operations of the driver.

5. The awakening support apparatus according to claim 4, wherein
the acquisition portion acquires the surroundings information indicating a first temperature around an upper portion of the driver and a second temperature around a lower portion of the driver,
the determination portion determines the drowsiness inducing level based on a temperature difference between the first temperature and the second temperature and the monotonicity index.

6. The awakening support apparatus according to claim 4, wherein
the acquisition portion acquires the surroundings information indicating the vibration around a shoulder blade and a sacrum of the driver,
the determination portion determines the drowsiness inducing level based on a combination of the vibration acquired by the acquisition portion and the monotonicity index.

7. The awakening support apparatus according to claim 4, wherein
the execution portion performs the awakening support correlated to the surroundings information in a case where it is determined that the surroundings information is greater than a first threshold value as the drowsiness inducing level and performs the awakening support correlated to the monotonicity index in a case where it is determined that the monotonicity index is greater than a second threshold value as the drowsiness inducing level.

8. An awakening support method comprising:
acquiring surroundings information which indicates information of a temperature around a driver of a movable object and a vibration applied to a specific portion of the driver;
determining a drowsiness inducing level of the driver based on an enhancement environmental index indicating a heat dissipation of the driver, enhancement environmental index being calculated on a basis of the temperature and the vibration included in the surroundings information; and
executing an awakening support for decreasing a possibility of induction of drowsiness of the driver based on a determination result of the drowsiness inducing level.

9. A computer program product including programed instructions embodied in and stored on a non-transitory computer readable medium, wherein the instructions, when executed by a computer, cause the computer to perform;
acquiring surroundings information which indicates information of a temperature around a driver of a movable object and a vibration applied to a specific portion of the driver;
determining a drowsiness inducing level of the driver based on an enhancement environmental index indicating a heat dissipation of the driver, enhancement environmental index being calculated on a basis of the temperature and the vibration included in the surroundings information; and
executing an awakening support for decreasing a possibility of induction of drowsiness of the driver based on a determination result of the drowsiness inducing level.

* * * * *